(12) United States Patent
Shekhawat et al.

(10) Patent No.: US 9,598,644 B1
(45) Date of Patent: Mar. 21, 2017

(54) METHOD OF CO AND/OR $CO_2$ HYDROGENATION TO HIGHER HYDROCARBONS USING DOPED MIXED-METAL OXIDES

(71) Applicants: Dushyant Shekhawat, Morgantown, WV (US); David A. Berry, Morgantown, WV (US); Daniel J. Haynes, Morgantown, WV (US); Victor Abdelsayed, Morgantown, WV (US); Mark W. Smith, Morgantown, WV (US); James J. Spivey, Baton Rouge, LA (US)

(72) Inventors: Dushyant Shekhawat, Morgantown, WV (US); David A. Berry, Morgantown, WV (US); Daniel J. Haynes, Morgantown, WV (US); Victor Abdelsayed, Morgantown, WV (US); Mark W. Smith, Morgantown, WV (US); James J. Spivey, Baton Rouge, LA (US)

(73) Assignee: U.S. Department of Energy, Washington, DC (US)

(*) Notice: Subject to any disclaimer, the term of this patent is extended or adjusted under 35 U.S.C. 154(b) by 0 days.

(21) Appl. No.: 14/834,487

(22) Filed: Aug. 25, 2015

Related U.S. Application Data

(63) Continuation-in-part of application No. 13/957,539, filed on Aug. 2, 2013, now Pat. No. 9,150,476.

(51) Int. Cl.
  *C10G 2/00* (2006.01)
(52) U.S. Cl.
  CPC .............. *C10G 2/333* (2013.01); *C10G 2/50* (2013.01)

(58) Field of Classification Search
  CPC . C10G 2/333; C10G 2/30; C10G 2/33; C10G 2/331; C10G 2/332; C10G 2/50;
  (Continued)

(56) References Cited

U.S. PATENT DOCUMENTS 4,126,580 A    11/1978 Lauder
4,312,955 A    1/1982 Bartley
(Continued)

OTHER PUBLICATIONS

Abdelsayed ("Synthesis, characterization, and catalytic activity of Rh-based lanthanum zirconate pyrochlores for higher alcohol synthesis" Catalysis Today, 207, 2013, p. 65-73).*

(Continued)

*Primary Examiner* — Jafar Parsa
*Assistant Examiner* — Amy C Bonaparte
(74) *Attorney, Agent, or Firm* — Karen L. Blouin; Michael J. Dobbs; Brian J. Lally

(57) ABSTRACT

A method of hydrogenation utilizing a reactant gas mixture comprising a carbon oxide and a hydrogen agent, and a hydrogenation catalyst comprising a mixed-metal oxide containing metal sites supported and/or incorporated into the lattice. The mixed-metal oxide comprises a pyrochlore, a brownmillerite, or mixtures thereof doped at the A-site or the B-site. The metal site may comprise a deposited metal, where the deposited metal is a transition metal, an alkali metal, an alkaline earth metal, or mixtures thereof. Contact between the carbon oxide, hydrogen agent, and hydrogenation catalyst under appropriate conditions of temperature, pressure and gas flow rate generate a hydrogenation reaction and produce a hydrogenated product made up of carbon from the carbon oxide and some portion of the hydrogen agent. The carbon oxide may be CO, $CO_2$, or mixtures thereof and the hydrogen agent may be $H_2$. In a particular embodiment, the hydrogenated product comprises olefins, paraffins, or mixtures thereof.

12 Claims, 1 Drawing Sheet

(58) Field of Classification Search
CPC .... C07C 1/00; C07C 1/02; C07C 1/04; C07C 1/0425; C07C 1/043; C07C 1/0435; C07C 1/12
See application file for complete search history.

(56) References Cited

U.S. PATENT DOCUMENTS

| | | | |
|---|---|---|---|
| 4,863,971 A | 9/1989 | Broussard et al. | |
| 5,105,053 A * | 4/1992 | Jacobson | B01J 23/005 502/324 |
| 5,714,091 A * | 2/1998 | Mazanec | B01D 53/228 252/373 |
| 6,033,632 A * | 3/2000 | Schwartz | B01D 53/228 210/500.25 |
| 6,409,940 B1 * | 6/2002 | Gaffney | B01J 23/8946 252/373 |
| 8,133,463 B1 * | 3/2012 | Berry | B01J 23/002 252/373 |
| 8,241,600 B1 * | 8/2012 | Berry | B01J 23/002 252/373 |
| 8,486,301 B2 * | 7/2013 | Berry | B01J 37/0236 252/373 |
| 2007/0142483 A1 * | 6/2007 | White | B01J 23/002 518/726 |
| 2009/0123354 A1 * | 5/2009 | Jan | C01B 3/386 423/263 |

OTHER PUBLICATIONS

Tien-Thao et al., "Effect of alkali additives over nanocrystalline Co—Cu-based perovskites as catalysts for higher-alcohol synthesis," Journal of Catalysis 245 (2007).

Tien-Thao et al., "Characterization and reactivity of nanoscale La(Co,Cu)O3 perovskite catalyst precursors for CO hydrogenation," Journal of Solid State Chemistry 181 (2008).

Kieffer et al., "Hydrogenation of CO and CO 2 toward methanol, alcohols and hydrocarbons on promoted copper-rare earth oxides catalysts," Catalysis Today 36 (1997).

Chu et al., "Conversion of syngas to C1-C6 alcohol mixtures on promoted CuLa2Zr2O7 catalysts," Applied Catalysis A: General 121 (1995).

Fujiwara et al., "Hydrogenation of carbon dioxide over copper-pyrochlore/zeolite composite catalysts," Catalysis Today 29 (1996).

Fang et al., "LaFeO3-supported nano Co—Cu catalysts for higher alcohol synthesis from syngas," Applied Catalysis A: General 397 (2011).

Chuang et al., "Mechanism of C2+ oxygenate synthesis on Rh catalysts," Topics in Catalysis 32 (2005).

Bourzutschky et al., "Conversion of synthesis gas over LaMn1-xCuxO3+λ perovskite and related copper catalysts," Journal of Catalysis 124 (1990).

* cited by examiner

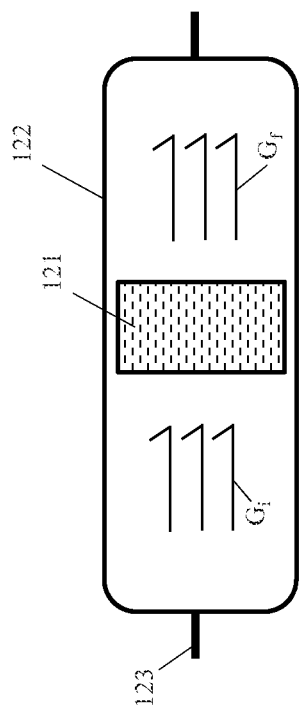

METHOD OF CO AND/OR $CO_2$ HYDROGENATION TO HIGHER HYDROCARBONS USING DOPED MIXED-METAL OXIDES

RELATION TO OTHER APPLICATIONS

This patent application is a continuation-in-part of and claims priority from nonprovisional patent application Ser. No. 13/957,539 filed Aug. 2, 2013, which is hereby incorporated by reference in its entirety.

GOVERNMENT INTERESTS

The United States Government has rights in this invention pursuant to the employer-employee relationship of the Government to the inventors as U.S. Department of Energy employees and site-support contractors at the National Energy Technology Laboratory.

FIELD OF THE INVENTION

One or more embodiments relates to a method of hydrogenation using a hydrogenation catalyst comprising a mixed-metal oxide containing metal sites supported on and/or incorporated into the lattice. In an embodiment, the metal site is a deposited metal and the mixed-metal oxide supports the metal site. The metal site comprises a transition metal, an alkali metal, an alkaline earth metal, or mixtures thereof, and the mixed-metal oxide comprises a pyrochlore, a brownmillerite, or mixtures thereof. The method of hydrogenation utilizes a reactant gas mixture comprising a carbon oxide such as CO or $CO_2$ and a hydrogen agent such as $H_2$ for the generation of various hydrogenated products, including olefins, paraffins, and others.

BACKGROUND

Hydrogenation catalysts, which enhance reactions between hydrogen and other compounds, are a topic of significant interest. In particular, catalysts for $CO/CO_2$ hydrogenations into higher hydrocarbons are of specific interest. These products are widely used as solvents, intermediates, fuel additives, and neat fuels, and producing these products selectively requires catalysts with specific properties. Typically, major byproducts from $CO/CO_2$ hydrogenations are single carbon compounds, so a major challenge is the development of catalysts with higher selectivity towards the higher chain hydrocarbons. There is particular emphasis on high selectivity catalysts for $CO/CO_2$ hydrogenations acting in environments of CO, $CO_2$, and $H_2$, such as syngas, which require relatively high stability in the presence of a reducing environment. Generally a variety of catalysts, particularly the Group 6 through 11 metals, have been employed in $CO/CO_2$ hydrogenations, but in many cases these catalysts generate broad, complex mixtures of hydrocarbons, oxygenated hydrocarbons, and carbon dioxide. Thus, there is a need for $CO/CO_2$ hydrogenation catalysts that selectively generate long-chain hydrocarbons products.

Certain metals such as Rh. Co, and Fe have been extensively studied because of their generally high hydrogenation activities. The activity and selectivity of the active metal catalysts can be increased by various factors, such as the presence of promoters, the choice of support, the synthesis method, the use of specific precursors, and other factors. Generally, optimum long-chain hydrocarbon formation requires a balance among the rates of CO dissociation, hydrogenation, and methyl group insertion. For example, promoters such as rare earth metals, alkali metals, and other transition metals play an important role in these elementary steps. Typically the promoters activate the oxygen atom of an absorbed CO molecule and weaken the C—O bond, leading to CO dissociation followed by a hydrogenation step to form $CH_x$ species. The mechanism for C—C bond formation leading to the formation of long-chain hydrocarbons also requires the atomic proximity of another activated $CH_x$ species. Subsequent insertion steps and hydrogenation of the initial $C_2$ intermediate leads to higher chain hydrocarbon synthesis. Catalytic metals have also been supported on certain crystalline oxides such as pyrochlores in an effort to promote selectivity in $CO/CO_2$ hydrogenations. $CO/CO_2$ hydrogenation catalysts have involved catalytic metals such as Co, Cu, and Rh supported by various structures such as $La_2Zr_2O_7$, $La_2FeO_3$, $La_2O_3$, $TiO_2$, $SiO_2$, and $Al_2O_3$. See Kieffer et al., "Hydrogenation of CO and $CO_2$ toward methanol, alcohols and hydrocarbons on promoted copperrare earth oxides catalysts," *Catalysis Today* 36 (1997); and see Chu et al., "Conversion of syngas to C1-C6 alcohol mixtures on promoted $CuLa_2Zr_2O_7$ catalysts." *Applied Catalysis A: General* 121 (1995); and see Fujiwara et al., "Hydrogenation of carbon dioxide over copper-pyrochlore/zeolite composite catalysts," *Catalysis Today* 29 (1996). The efforts are generally aimed toward adjustment of the CO dissociation and insertion abilities of the Co, Cu, or Rh through varying promoter and support compositions. Variations in selectivities are typically attributed to the specific properties of the support, the promoter, the morphology of the metal, and the impact of the support on the reducibility of the metal.

Provided here is a method of hydrogenation utilizing a reactant gas mixture comprising a carbon oxide and a hydrogen agent, and a hydrogenation catalyst comprising a mixed-metal oxide with a metal site supported by and/or incorporated into the lattice. In an embodiment, the metal site is a deposited metal and the mixed-metal oxide supports the metal site. The metal site comprises a transition metal, an alkali metal, an alkaline earth metal, or mixtures thereof, and the conducting oxide comprises a pyrochlore, a brownmillerite, or mixtures thereof, typically doped at an A-site or B-site of the conducting oxide crystal structure. Contact between the carbon oxide, hydrogen agent, and hydrogenation catalyst under appropriate conditions of temperature, pressure and gas flow rate generate a reaction and products comprising paraffins, olefins, or combinations thereof, where the paraffins, olefins, or combinations comprise carbon from the carbon oxide and some portion of the hydrogen agent. The carbon oxide may be CO, $CO_2$, or mixtures thereof and the hydrogen agent may be $H_2$.

These and other objects, aspects, and advantages of the present disclosure will become better understood with reference to the accompanying description and claims.

SUMMARY

The method generally entails contacting a reactant gas mixture comprising a carbon oxide and a hydrogen agent with a hydrogenation catalyst, where the hydrogenation catalyst comprises a mixed-metal oxide containing metal sites that can be supported and/or incorporated into the lattice. In certain embodiments, the metal sites comprise a deposited metal supported by the mixed-metal oxide, and the deposited metal is a transition metal, an alkali metal, an alkaline earth metal, or mixtures thereof. In certain embodiments, the carbon oxide is CO. $CO_2$, or mixtures thereof and the hydrogen agent is $H_2$. The mixed-metal oxide comprises a pyrochlore or a brownmillerite, typically doped at an A-site or B-site of the mixed-metal oxide crystal structure. The A-site and B-site dopants are typically present at lattice points of the crystal structure of the mixed-metal oxide, and coordinated with oxygen atoms in the crystal structure of the mixed-metal oxide. In some embodiments, the A-site or B-site comprises a noble metal. In additional embodiments, the metal site comprises a deposited metal deposited on the mixed-metal oxide and comprises a noble metal.

Contact between the carbon oxide, hydrogen agent, and hydrogenation catalyst generates a hydrogenation reaction and produces a hydrogenated product made up of carbon from the carbon oxide and some portion of the hydrogen agent. In a particular embodiment, the hydrogenated product comprises paraffins, olefins, small quantities of oxygenated hydrocarbons, or mixtures thereof.

The various mixed-metal oxides described interact with the metal sites to form products from reactant gas mixtures such as syngas with a high degree of selectivity. A feature of the mixed-metal oxides utilized here is the ability to isomorphically substitute into the structure various catalytically active elements that can interact at the surface with clusters of metal atoms. Small clusters of metallic sites deposited onto the mixed-metal oxide containing structurally incorporated metallic sites provides the unique ability to tailor the distribution of active sites in order to improve product selectivity. Additionally, the ability to provide multiple dopants into the mixed-metal oxides described allow advantageous use of the bifunctional base-hydrogenation catalysts generally used for $CO/CO_2$ hydrogenations. The basic sites may act to catalyze the condensation reaction by activating adsorbed CO, e.g., by enhancing the formation of the formate intermediate which can be hydrogenated into methyl groups leading to higher chain hydrocarbon growth.

The materials can be processed via a number of synthesis methods including but not limited to solid state diffusion, polymeric precursor method (e.g. Pechini Method), combustion synthesis, co-precipitation, hydrothermal, solgel, citric acid method, chemical vapor deposition, atomic layer deposition, and other means known in the art for synthesis of metal sites with mixed-metal oxides as described herein.

The novel process and principles of operation are further discussed in the following description.

BRIEF DESCRIPTION OF THE DRAWINGS

The FIGURE illustrates an embodiment of the method of conducting the hydrogenation process.

DETAILED DESCRIPTION

The following description is provided to enable any person skilled in the art to use the invention and sets forth the best mode contemplated by the inventors for carrying out the invention. Various modifications, however, will remain readily apparent to those skilled in the art, since the principles of the present invention are defined herein specifically to provide a method of conducting a hydrogenation process with a carbon oxide, a hydrogen agent, and a hydrogenation catalyst comprising a mixed-metal oxide and metal sites as described herein to produce olefins, paraffins, and combinations thereof comprising carbon from the carbon oxide and some portion of the hydrogen agent.

The method generally entails contacting a reactant gas mixture comprising a carbon oxide and a hydrogen agent with a hydrogenation catalyst, where the hydrogenation catalyst comprises a mixed-metal oxide containing metal sites supported by and/or incorporated into the lattice. The mixed-metal oxide comprises a pyrochlore, a brownmillerite, or mixtures thereof, typically doped at an A-site or B-site of the mixed-metal oxide crystal structure. In certain embodiments, the metal sites comprise a deposited metal supported by the mixed-metal oxide, and the deposited metal is a transition metal, an alkali metal, an alkaline earth metal, or mixtures thereof. Contact between the carbon oxide, hydrogen agent, and hydrogenation catalyst under appropriate conditions of temperature, pressure and gas flow rate generate a hydrogenation reaction and produce a hydrogenated product made up of carbon from the carbon oxide and some portion of the hydrogen agent. The carbon oxide may be CO, $CO_2$, or mixtures thereof. In certain embodiments, the hydrogen agent is $H_2$. Contact between the reactant gas mixture and the hydrogenation catalyst generates reaction products comprising a hydrogenation product of paraffins, olefins, or mixtures thereof. In a particular embodiment, the reaction products have at least 15% product selectivity, preferably at least 30% product selectivity, more preferably at least 50% product selectivity for the hydrogenation product of paraffins, olefins, or mixtures thereof. In another embodiment, the reaction products have a less than 20% product selectivity, preferably less than 15% product selectivity, more preferably less than 10% product selectivity for oxygenated hydrocarbons.

In general embodiments, the mixed-metal oxide is doped with an A-site dopant, a B-site dopant, or a combination of A-site and B-site dopants. The A-site and B-site dopants are present at lattice points of the crystal structure of the mixed-metal oxide, and coordinated with oxygen atoms in the crystal structure of the mixed-metal oxide. In another embodiment, the A-site or B-site comprises a noble metal. In a further embodiment, the metal sites comprise a deposited metal deposited on the mixed-metal oxide. In another embodiment, the metal site comprises a noble metal, and in a further embodiment, the deposited metal comprises a noble metal.

The structure of the various mixed-metal oxides described interacts with the metal sites to form products from reactant gas mixtures such as syngas with a high degree of selectivity. Generally and without being bound by theory, the effectiveness of catalysts based on metals such as Rh for the formation of products such as $C_{2+}$ and higher chain hydrocarbons are greatly improved through interaction with the mixed-metal oxide and atomically adjacent promoters.

A feature of the mixed-metal oxides utilized here is the ability to isomorphically substitute into the structure various elements that can interact at the surface with clusters of metal atoms. The properties of the mixed-metal oxide can be used to tailor the degree and type of interaction with an active metal comprising the metal site to catalyze the conversion of syngas to specific end products. Small clusters of metallic sites deposited onto the mixed-metal oxide containing structurally incorporated metallic sites provides the unique ability to tailor the distribution of active sites in order to improve product selectivity. In an embodiment, a ratio (S/Y) is at least 1, preferably at least 10, more preferably at least 100, where S is the number of catalytically active surface sites deposited onto a mixed-metal oxide, and Y is the number of catalytically active sites substituted as B' dopants into the mixed-metal oxide. The number of catalytically active sites on the surface (S) and substituted into the B-site of the mixed-metal oxide (Y) can be determined using one of several well-known characterization techniques (e.g. $H_2$ or CO chemisorption, temperature programmed desorption, SEM, XPS, etc.). Additionally, the ability to provide multiple dopants into the mixed-metal oxides described allow advantageous use of the bifunctional base-hydrogenation catalysts generally used for $CO/CO_2$ hydrogenations. The basic sites may act to catalyze the condensation reaction by activating adsorbed CO, e.g., by enhancing the formation of the formate intermediate which can be hydrogenated into methyl groups leading to higher chain hydrocarbon growth. The pyrochlore and brownmillerite materials described here have the ability to incorporate both functionalities by substituting a base at the A-site and hydrogenation catalyst at the B-site.

These catalysts, comprising a metal site with a typically doped pyrochlore, brownmillerite, or mixtures thereof, can be utilized in a variety of forms including but not limited to powders, pellets, foam catalysts, monolithic catalysts, wall-deposited (tubular or planar), deposited fiber, or any other geometric shape catalyst system. The pyrochlore and brownmillerite materials described allow substituted materials to modify the pyrochlore and brownmillerite materials and interact with the metal sites in a variety of specific, different manners, through the availability of a wide range of catalytically active metals, which can be supported on or substituted into the pyrochlore and brownmillerite materials.

The materials can be processed via a number of synthesis methods including but not limited to solid state diffusion, polymeric precursor method (e.g. Pechini Method), combustion synthesis, co-precipitation, hydrothermal, solgel, citric acid method, chemical vapor deposition, atomic layer deposition, and other means known in the art for synthesis of mixed-metal oxides containing deposited and/or substituted metal sites as described herein.

Here, "carbon oxide" means CO, $CO_2$, or mixtures thereof. "Hydrogen agent" means a material comprising hydrogen which donates hydrogen when the carbon oxide and the hydrogen agent contact the hydrogenation catalyst under the temperature, pressure and gas flow rate conditions sufficient to produce a hydrogenated product made up of some portion of the carbon oxide and some portion of the hydrogen agent. The hydrogen agent may be $H_2$ or may be a material commonly considered a hydrogen-transfer agent in hydrogenation processes, such as hydrazine, dihydronaphthalene, dihydroanthracene, isopropanol, formic acid, and others. See e.g., Brieger et al., "Catalytic Transfer Hydrogenation," *Chemical Reviews* 74(5) (1974), among others. Additionally, while the carbon oxide and the hydrogen agent comprise the reactant gas mixture, the reactant gas mixture may further comprise other constituents. For example, the reactant gas mixture may further comprise paraffins, olefins, oxygenated hydrocarbons, and other compounds.

"Hydrogenated product" means a material comprising carbon and hydrogen where at least some portion of the carbon is derived from the carbon oxide and where at least some portion of the hydrogen is derived from the hydrogen agent. A "hydrogenation reaction" means a reaction in the presence of the hydrogenation catalyst where carbon derived from the carbon oxide and hydrogen derived from the hydrogen agent serve as reactants in a reaction producing the hydrogenated product. "Reaction product" means products comprising the hydrogenated product. In an embodiment, reaction products have at least 15% product selectivity, preferably at least 30% product selectivity, more preferably at least 50% product selectivity for paraffins, olefins, of combinations thereof. In another embodiment, the reaction products have a less than 20% product selectivity, preferably less than 15% product selectivity, more preferably less than 10% product selectivity for oxygenated hydrocarbons.

"Metal site" means a metal element deposited onto and supported by the mixed-metal oxide, or an atomically substituted metal element. The metal site may be an A-site or B-site dopants occupying a lattice point of the pyrochlore or brownmillerite crystal structure of the mixed-metal oxide, or the metal site may be a deposited metal which does not occupy a lattice point of the pyrochlore or brownmillerite crystal structure of the mixed-metal oxide. Metal site as used here may refer to a single element or may refer to chemical entities such as mixtures and alloys comprising multiple elements, or may refer to a group of elements comprising the hydrogenation catalyst where the elements in the group comprise an A-site dopant, a B-site dopant, a deposited metal, or some combination therein.

"Deposited metal" means a deposit comprising a metal and affixed to the conducting oxide, where the metal comprises a transition metal, an alkali metal, an alkaline earth metal, or mixtures thereof. As a deposited site and unlike the A-site of B-site dopants when present, the metal site does not occupy a lattice point of the pyrochlore or brownmillerite crystal structure of the conducting oxide. In a particular embodiment, deposited metals are present such that a ratio (S/Y) is at least 1, preferably at least 10, and more preferably at least 100, where S is the number of catalytically active surface sites deposited onto a mixed-metal oxide and Y is the number of catalytically active sites substituted as B' dopants in the mixed-metal oxide. The number of catalytically active sites on the surface (S) and substituted into the B-site of the mixed-metal oxide (Y) can be determined using one of several well-known characterization techniques (e.g. $H_2$ or CO chemisorption, temperature programmed desorption, SEM, XPS, etc.). See e.g. Abdelsayed et al., "Synthesis, characterization, and catalytic activity of Rh-based lanthanum zirconate pyrochlores for higher alcohol synthesis," *Catalysis Today* 207 (2013); See also Haynes et al., "Catalytic partial oxidation of n-tetradecane using pyrochlores: Effect of Rh and Sr substitution," *Catalysis Today* 136 (2008); see also Linder et al., "Chemisorption Studies of Promoted Solid-State HDS Catalysts," *Journal of Catalysis* 135 (1992); see also Qian et al., "Catalytically Active Structures of $SiO_2$-supported Au nanoparticles in low temperature CO oxidation," *Catal. Sci. Technol* 3(3) (2013); see also J. L. G. Fierro, *Spectroscopic Characterization of Heterogeneous Catalysts Part B: Chemisoprtion of Probe Molecules* (1990).

"Transition metal" means the chemical elements with atomic numbers 21 to 30, 39 to 48, 71 to 80, and 103 to 109.

"Alkali metal" means the chemical elements Li, Na, K, Rb, Cs, and Fr.

"Alkaline earth metal" means the chemical elements Be, Mg, Ca, Sr, Ba, and Ra.

"Noble metal" is a subset of transition metal as used herein and means the chemical elements Ru, Rh, Pd, Ag, Os, Ir, Pt, and Au.

"Lanthanide series metal" means the chemical elements with atomic numbers 57 through 71 consisting of La, Ce, Pr, Nd, Pm, Sm, Eu, Gd, Tb, Dy, Ho, Er, Tm, Yb, Lu. Further, a "Group N metal" where N is a number from 1 to 18 refers to an element within the collection of elements that make up a Group designated with the number N as described by the International Union of Pure and Applied Chemistry (IUPAC). Additionally, when a second element is "not equivalent" to a first element, this means the second element has an atomic number on the IUPAC periodic table which is not equal to the first element. Similarly, when a second element is "equivalent" to a first element, this means the second element has an atomic number on the IUPAC periodic table which is equal to the first element.

The terms "paraffin," "olefin," and "oxygenated hydrocarbons" describe organic molecules and are known in the art. "Oxygenated hydrocarbons" used as another class of compound indicates the presence of an oxygen at any position in the hydrocarbon chain. Generally, "oxo" used as an adjective to modify another class of compound indicates the presence of an oxo substituent at any position. See e.g. IUPAC, *Commission on Nomenclature of Organic Chemistry. A Guide to IUPAC Nomenclature of Organic Compounds (Recommendations 1993)*, 1993, Blackwell Scientific publications, and see "Corrections to A Guide to IUPAC Nomenclature of Organic Compounds," *Pure Appl. Chem.*, 71 (1999). Additionally within this disclosure, chemical symbols and atomic numbers signify elements designated by like chemical symbols and atomic numbers according to The 2012 IUPAC (International Union of Pure and Applied Chemistry) Periodic Table of The Elements.

Within this method, the reactant gas mixture and the hydrogenation catalyst may be contacted and maintained at conditions of temperature, pressure and gas flow rate sufficient to generate a hydrogenation reaction and produce the hydrogenated product using any means known in the art. For example, the hydrogenation catalyst may be contained within a reactor volume maintained at a specific temperature and pressure and the reactant gas mixture may be introduced into the reactor volume at a rate sufficient to establish a specific gas flow rate over the hydrogenation catalyst, and the hydrogenated product may be withdrawn from the reactor volume. In an embodiment, the hydrogenation process occurring within the reactor volume is an exothermic process, and heat is withdrawn from the reactor volume to maintain the specific temperature and pressure. The sufficiency of the temperature, pressure and gas flow rate conditions may entail any combination of temperature, pressure and gas flow rate provided that contacting the reactant gas mixture and the hydrogenation catalyst generates the hydrogenation reaction and produces the hydrogenated product.

In an embodiment, the mixed-metal oxide includes a doped pyrochlore having the pyrochlore composition $A_{2-x}A'_xB_{2-y}B'_yO_{7-z}$, where A is one or more of a lanthanide series metal or Ca, A' if present is one or more of a Group 1 metal, a Group 2 metal, or mixtures thereof, B is one or more of a transition metal, B' if present is one or more of a noble metal, and O is the element oxygen. In this embodiment, A' is not equivalent to A, B' is not equivalent to B, and $0 \le x \le 1$, $0 \le y \le 1$, and $x+y>0$, such that the A-site, the B-site, or both are doped, and z is a number that renders the composition charge neutral. In another embodiment, A' if present is an A-site dopant at a lattice point of the pyrochlore crystal structure, and B' if present is a B-site dopant at another lattice point of the pyrochlore crystal structure, and A' and B' when present are coordinated with oxygen atoms in the pyrochlore crystal structure. In another embodiment, the hydrogenation catalyst comprises the doped pyrochlore having the pyrochlore composition $A_{2-x}A'_xB_{2-y}B'_yO_{7-z}$ and a deposited metal on the doped pyrochlore, where the deposited metal comprises a transition metal, an alkali metal, an alkaline earth metal, or mixtures thereof.

Generally, in a pyrochlore composition $A_{2-x}A'_xB_{2-y}B'_yO_{7-z}$ having a pyrochlore crystal structure, the pyrochlore is composed of ½ trivalent cations and ½ tetravalent cations in a cubic cell structure. The A-site is usually a large cation (typically rare earth elements) and is coordinated with eight oxygen atoms. The B-site cation has a smaller radius (usually transition metal) and is coordinated with six oxygen atoms. The necessary ionic states, ionic radii, and oxygen atom coordination generally necessary to form a pyrochlore crystal structure are known in the art. See e.g. Subramanian et al, "Oxide Pyrochlores—A Review," *Progress in Solid State Chemistry*, 15 (1983), among others.

In a particular embodiment where the mixed-metal oxide includes the pyrochlore composition $A_{2-x}A'_xB_{2-y}B'_yO_{7-z}$, A is one of La, Ce, Gd, or mixtures thereof and B is one of Ti, V, Cr, Mn, Cu, Y, Co, Fe, Mo, Ni or mixtures thereof. In this embodiment, A' if present is one of Ca, Sr, Ba or mixtures thereof and B' if present is Rh, Ru, or mixtures thereof. In another embodiment, both x and y are greater than zero such that the doped pyrochlore has both an A-site dopant and a B-site dopant. In a further embodiment, the A-site or B-site dopant comprises a metal equivalent to a metal comprising a deposited metal supported by the mixed-metal oxide. In a further embodiment, y>0 and B' is a first noble metal, and the deposited metal supported by the doped pyrochlore comprises a second noble metal. In a still further embodiment, the second noble metal is equivalent to the first noble metal. Additionally, when the hydrogenation catalyst comprises the doped pyrochlore, the hydrogenation catalyst may additionally comprise other crystal phases, including simple oxides, weberites, and others. Further, the doped pyrochlore comprising the hydrogenation catalyst may be either self-supported or structurally supported on a substrate such as aluminas, silicas, other oxides, and other substrates known in the art, and combinations thereof.

In another embodiment, the mixed-metal oxide includes a doped brownmillerite having the brownmillerite composition $A_{2-x}A'_xB_{2-y}B'_yO_{5-z}$ where A is one or more of an alkaline earth metal, A' if present is one or more of a lanthanide series metal, Group 3 metal, or mixtures thereof, B is one or more of a transition metal, a Group 13 metal, or mixtures thereof, B' if present is one or more of a lanthanide series metal, a noble metal, a Group 3 metal, or mixtures thereof, and O is the element oxygen. In this embodiment, A' is not equivalent to A, B' is not equivalent to B, and $0 \le x \le 1$, $0 \le y \le 1$, and $x+y>0$, such that the A-site, the B-site, or both are doped, and z is a number that renders the composition charge neutral. In an embodiment, A' if present is an A-site dopant at a lattice point of the brownmillerite crystal structure, and B' if present is a B-site dopant at another lattice point of the brownmillerite crystal structure, and A' and B' when present are coordinated with oxygen atoms in the brownmillerite crystal structure. In another embodiment, the hydrogenation catalyst comprises the doped brownmillerite having the brownmillerite composition $A_{2-x}A'_xB_{2-y}B'_yO_{5-z}$ and a deposited metal on the doped brownmillerite, where the deposited metal comprises a transition metal, an alkali metal, an alkaline earth metal, or mixtures thereof.

Generally, in a brownmillerite composition $A_{2-x}A'_xB_{2-y}B'_yO_{5-z}$ having a brownmillerite crystal structure, the A-site and B site cations are statistically distributed and coordinated with oxygen anions in both octahedral and tetrahedral sites. Brownmillerites are closely related to perovskites and generally have layers of corner sharing $BO_6$ octahedra are separated by chains of corner sharing $BO_4$ tetrahedra. The necessary ionic states, ionic radii, and oxygen atom coordination generally necessary to form a brownmillerite crystal structure are known in the art. See e.g., Ramezanipour et al., "Intralayer Cation Ordering in a Brownmillerite Superstructure: Synthesis, Crystal, and Magnetic Structures of $Ca_2FeCoO_5$," *Chem. Mater.* 22 (2010), among others.

In a particular embodiment where the mixed-metal oxide includes the brownmillerite composition $A_{2-x}A'_xB_{2-y}B'_yO_{5-z}$, A is one of Ca, Sr, Ba, or mixtures thereof and B is one of Al, Ga, In, Ti, V, Cr, Mn, Cu, Co, Ni or mixtures thereof. In this embodiment, A' if present is one of La, Ce, Gd, Y or mixtures thereof and B' if present is one of Rh, Ru, Y, or mixtures thereof. In another embodiment, both x and y are greater than zero such that the doped brownmillerite has both an A-site dopant and a B-site dopant. In a further embodiment, the A-site or B-site dopant comprises a metal equivalent to a metal comprising a deposited metal supported by the mixed-metal oxide. In a further embodiment, y>0 and B' is a first noble metal, and the deposited metal supported by the doped brownmillerite comprises a second noble metal. In a still further embodiment, the second noble metal is equivalent to the first noble metal. Additionally, when the hydrogenation catalyst comprises the doped brownmillerite, the hydrogenation catalyst may additional comprise other crystal phases, including simple oxides, weberites, and others. Further, the doped brownmillerite comprising the hydrogenation catalyst may be either self-supported or structurally supported on a substrate such as aluminas, silicas, other oxides, and other substrates known in the art, and combinations thereof.

In a particular embodiment, the carbon oxide is CO, $CO_2$, or mixtures thereof, the hydrogen agent is $H_2$, and the hydrogenated product comprises a paraffin, an olefin, or mixtures thereof. In another embodiment where the carbon oxide is CO, $CO_2$, or mixtures thereof and the hydrogen agent is $H_2$, the reactant gas mixture has $H_2$ to carbon oxide ratio from 1 to 10, and the reactant gas mixture and the hydrogenation catalyst are contacted at a temperature from 50° C. to 500° C., a pressure from 1 atmosphere to 400 atmospheres, and a gas flow rate from 10 scc/gcat/h to 100,000 scc/gcat/h, and the hydrogenated product comprises an alcohol, an olefin, or mixtures thereof. In another embodiment where the carbon oxide is CO, $CO_2$, or mixtures thereof and the hydrogen agent is $H_2$, the reactant gas mixture has $H_2$ to carbon oxide ratio from 1 to 10, and the reactant gas mixture and the hydrogenation catalyst are contacted at a temperature from 30° C. to 400° C., a pressure from 1 atmosphere to 400 atmospheres, and a gas flow rate from 0.1 scc/gcat/h to 100 scc/gcat/h, and the hydrogenated product comprises paraffins, olefins, oxygenated hydrocarbons, or mixtures thereof.

A particular use of the hydrogenation catalyst is illustrated at the FIGURE. At the FIGURE, hydrogenation catalyst 121 resides in a packed bed within a hydrogenation reactor 122. Hydrogenation catalyst 121 comprises a mixed-metal oxide, where the mixed-metal oxide is a doped pyrochlore or a doped brownmillerite, or mixtures thereof, as described herein. In an embodiment, hydrogenation catalyst 121 comprises the mixed-metal oxide supporting a deposited metal, where the deposited metal is a transition metal, an alkali metal, an alkaline earth metal, or mixtures thereof. A reactant gas mixture $G_i$ enters hydrogenation reactor 122 through inlet 123 and contacts hydrogenation catalyst 121 within hydrogenation reactor 122. Reactant gas mixture $G_i$ comprises a carbon oxide and a hydrogen agent. Hydrogenation reactor maintains reactant gas mixture $G_i$ and hydrogenation catalyst 121 at conditions of temperature, pressure and gas flow rate to generate a hydrogenation reaction and produce the reaction product $G_f$. Reaction product $G_f$ comprises a hydrogenated product, where the hydrogenated product comprises carbon from the carbon oxide and at least some portion of the hydrogen agent, and where the reaction product $G_f$ has at least a 15% product selectivity for paraffins, olefins, or mixtures thereof. In another embodiment, the reaction product $G_f$ has less than a 20% product selectivity for oxygenated hydrocarbons.

In an embodiment, the carbon oxide is CO, $CO_2$, or mixtures thereof and the hydrogen agent is $H_2$. In an additional embodiment, the hydrogenated product comprising reaction product $G_f$ is the paraffin, the olefin, or mixtures thereof, and the temperature during the contacting is from 50° C. to 500° C., the pressure during the contacting is from 1 atmosphere to 400 atmospheres, and reactant gas mixture $G_i$ has $H_2$ to carbon oxide ratio from 1 to 10 and reactant gas mixture $G_i$ contacts hydrogenation catalyst 121 at a gas flow rate sufficient to generate a Weight Hourly Space Velocity (WHSV) from 10 scc/gcat/h (standard cubic centimeters/grams catalyst/hour) to 100,000 scc/gcat/h. In another embodiment, the hydrogenated product comprising reaction product $G_f$ are the paraffins, olefins, oxygenated hydrocarbons, or mixtures thereof, and the temperature during the contacting is from 30° C. to 400° C., the pressure during the contacting is from 1 atmosphere to 400 atmospheres, and reactant gas mixture Gi has $H_2$ to carbon oxide ratio from 1 to 10 and reactant gas mixture $G_i$ contacts hydrogenation catalyst 101 at a gas flow rate sufficient to generate a WHSV from 0.1 scc/gcat/h to 100 scc/gcat/h.

DESCRIPTION OF SPECIFIC EMBODIMENTS

Catalyst Preparation:

Hydrogenation catalysts may be prepared using the Pechini Method. See U.S. Pat. No. 3,330,697 issued to Pechini, issued Jul. 11, 1967; see also Abdelsayed et al., "Synthesis, characterization, and catalytic activity of Rh-based lanthanum zirconate pyrochlores for higher alcohol synthesis," *Catalysis Today* 207 (2013). Sources of the metal cations A, A', B, or B' include compounds of those cations and mixtures thereof. An exemplary preparation method follows.

Pyrochlore Synthesis:

Metal nitrate precursors and citric acid are dissolved separately into deionized water. The citric acid/metal molar ratio may be from 1.0-1.5, preferably about 1.2. The aqueous metal salts are then combined into one beaker and stirred. The aqueous citric acid is then added to the combined metal salt solution. This solution is heated to 60-80° C., preferably about 70° C., with continuous stirring. Ethylene glycol (EG) is then added to the heated solution. The ethylene glycol/citric acid molar ratio may be from 1.0-4.0, preferably about 1.0. The solution is stirred continuously at the desired temperature for several hours to evaporate the majority of the water and to accelerate polymerization between metal-chelated citric acid and ethylene glycol. A clear viscous gel is obtained, which is further heated at 130° C. in a heating mantle until an amorphous polyester-type resin is obtained. The solid material is collected and calcined at 700-1200° C., preferably about 1000° C., for 4-12 hours, preferably about 8 hours, to breakdown the organic polymer and burns the carbon off leading to a highly crystalline mixed metal oxide.

Rh-Deposited Pyrochlores:

Microwave-assisted chemical reduction method is used to deposit 2 wt % Rh on the surface of either pure or Rh-substituted lanthanum zirconate (LZ)-pyrochlore catalysts (prepared by modified Pechini method mentioned under pyrochlore synthesis). In a typical procedure, rhodium nitrate is dissolved in a 100 ml of a $H_2O$:EtOH (1:2) mixture such that the Rh metal content is equivalent to 2 wt % Rh. The LZ powder is dispersed in the above mentioned solution for 3 hours. Next hydrazine monohydrate (500 µl) is added quickly under vigorous stirring at room temperature. The solution is kept under stirring for another hour before being transferred into a sealed Teflon vessel and placed on a turntable tray of an Anton Paar microwave reaction system (Synthos 3000) equipped with pressure and temperature sensors. The dispersion is microwaved for 5 min under continuous stirring and 800 W of microwave power. After cooling the dispersion, the particles are separated by centrifuge, washed with ethanol, and dried under vacuum at $10^{-3}$ Torr for 48 hours. After drying, the Rh-deposited pyrochlore catalyst is calcined at 400-600° C., preferably about 500° C., in air for 2-5 hours, preferably about 3 hours.

Microwave-assisted chemical reduction method, which is very different from conventional impregnation methods, offers fast and size-controlled particle nucleation and deposition on catalytic supports. Microwave irradiation (MWI) provides a fast dielectric heating to the reaction mixture, due to the difference in the reactant and solvent dielectric constants, leading to enhancement in the reduction rate of Rh nitrate by hydrazine hydrate. A microwave-induced homogeneous nucleation of metal clusters is intended to produce a narrow size distribution of Rh on the catalyst support.

It will be apparent to those skilled in the art that the foregoing preparation methods are presented by way of example only. Various alterations, improvements, and modifications to the presented preparation methods are within the scope and spirit of the present disclosure.

Thus, presented here is a method of hydrogenation where a reactant gas mixture comprising a carbon oxide and a hydrogen agent is contacted with a hydrogenation catalyst, where the hydrogenation catalyst comprises a mixed-metal oxide containing metal sites supported and/or incorporated into the lattice. The mixed-metal oxide comprises a, a pyrochlore, a brownmillerite, or mixtures thereof. Contact between the carbon oxide, hydrogen agent, and hydrogenation catalyst under appropriate conditions of temperature, pressure and gas flow rate generate a hydrogenation reaction and produce a hydrogenated product made up of carbon from the carbon oxide and some portion of the hydrogen agent. The carbon oxide may be CO, $CO_2$, or mixtures thereof. In certain embodiments, the hydrogen agent is $H_2$. In a particular embodiment, the hydrogenated product comprises paraffins, olefins, oxygenated hydrocarbons, or mixtures thereof. It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

What is claimed is:

1. A method of conducting a reaction process comprising:
   delivering a reactant gas mixture comprising a carbon oxide and a hydrogen agent;
   providing a catalyst comprising a deposited metal supported on a mixed-metal oxide, wherein the deposited metal comprises a transition metal, an alkali metal, an alkaline earth metal, a noble metal, or mixtures thereof, and wherein the mixed-metal oxide comprises a doped pyrochlore, a doped brownmillerite, or mixtures thereof wherein:
   the doped pyrochlore has a pyrochlore composition $A_{2-x}A'_xB_{2-y}B'_yO_{7-z}$ wherein,
      A is one or more of a lanthanide series metal, Ca, or mixtures thereof,
      A' is one or more of a Group 1 metal, a Group 2 metal, or mixtures thereof,
      B is one or more of a transition metal, Si, Ge, Sn, Pb, Ce, or mixtures thereof,
      B' is one or more of a noble metal and,
      $0 \leq x \leq 1$, $0 < y \leq 1$, $x+y > 0$, and z is a number that renders the composition charge neutral,
   the doped brownmillerite has a brownmillerite composition $A_{2-x}A'_xB_{2-y}B'_yO_{5-z}$ wherein,
      A is one or more of an alkaline earth metal,
      A' is one or more of a lanthanide series metal, a Group 3 metal, or mixtures thereof,
      B is one or more of a transition metal, a Group 13 metal, or mixtures thereof,
      B' is one or more of a lanthanide series metal, a noble metal, a Group 3 metal, or mixtures thereof and,
      $0 \leq x \leq 1$, $0 < y \leq 1$, $x+y > 0$, and z is a number that renders the composition charge neutral; and
   contacting the reactant gas mixture and the catalyst and maintaining the reactant gas mixture and the catalyst at conditions of temperature, pressure and gas flow rate to generate a reaction and produce a reaction product, the reaction product comprising carbon from the carbon oxide and at least some portion of the hydrogen agent, and the reaction product having at least a 15% product selectivity for the paraffins, olefins, or mixtures thereof and having less than a 20% product selectivity for oxygenated hydrocarbons, wherein a ratio S/Y is at least 10, where S is a number of catalytically active surface sites deposited onto the mixed-metal oxide, and Y is a number of catalytically active sites present as B' in the mixed-metal oxide.

2. The method of claim 1 wherein the reaction product has at least a 50% product selectivity for the paraffins, olefins, or mixtures thereof.

3. The method of claim 1 wherein the reaction product has less than a 10% product selectivity for oxygenated hydrocarbons.

4. The method of claim 1 wherein the mixed-metal oxide is the doped pyrochlore having the pyrochlore composition $A_{2-x}A'_xB_{2-y}B'_yO_{7-z}$ in a pyrochlore crystal structure, and wherein if x>0 then A' is an A-site dopant at a lattice point of the pyrochlore crystal structure and A' is coordinated with oxygen atoms in the pyrochlore crystal structure, and wherein if y>0 then B' is a B-site dopant at another lattice point of the pyrochlore crystal structure and B' is coordinated with oxygen atoms in the pyrochlore crystal structure, wherein A is one of La, Ca, Gd, or mixtures thereof, wherein if x>0 then A' is one of Ca, Sr, Ba or mixtures thereof, wherein B is one of Ti, V, Cr, Mn, Cu, Y, Co, Fe, Mo, Ni, Zr, Tc, Pd, Re, Hf, Os, Ir, Pt, Si, Ge, Sn, Pb, Ce, or mixtures thereof, and wherein if y>0 then B' is one of Rh, Ru, or mixtures thereof wherein x>0 and y>0.

5. The method of claim 1 wherein the mixed-metal oxide is the doped brownmillerite having the brownmillerite composition $A_{2-x}A'_xB_{2-y}B'_yO_{5-z}$ in a brownmillerite crystal structure, and wherein if x>0 then A' is an A-site dopant at a lattice point of the brownmillerite crystal structure and A' is coordinated with oxygen atoms in the brownmillerite crystal structure, and wherein if y>0 then B' is a B-site dopant at another lattice point of the brownmillerite crystal structure and B' is coordinated with oxygen atoms in the brownmillerite crystal structure.

6. The method of claim 5 wherein A is one of Ca, Sr, Ba or mixtures thereof, and wherein if x>0 then A' is one of La, Ce, Gd, Y or mixtures thereof, B is one of Al, Ga, In, Ti, V, Cr, Mn, Cu, Co, Ni or mixtures thereof, and wherein if y>0 then B' is one of Rh, Ru, Y or mixtures thereof.

7. The method of claim 6 wherein x>0 and y>0.

8. The method of claim 5 wherein y>0 and wherein B' is a first noble metal and wherein the deposited metal comprises a second noble metal, wherein the first noble metal is either equivalent to the second noble metal or not equivalent to the second noble metal.

9. The method of claim 8 wherein the first noble metal is equivalent to the second noble metal.

10. The method of claim 1 wherein the carbon oxide is CO, $CO_2$, or mixtures thereof and wherein the hydrogen agent is $H_2$.

11. The method of claim 10 wherein the temperature is from 50° C. to 500° C., the pressure is from 1 atmosphere to 400 atmospheres, wherein the reactant gas mixture has an $H_2$ to carbon oxide ratio from 1 to 10, and wherein the gas flow rate generates a Weight Hourly Space Velocity from 10 scc/gcat/h to 100,000 scc/gcat/h.

12. The method of claim 10 wherein the temperature is from 30° C. to 400° C., the pressure is from 1 atmosphere to 400 atmospheres, wherein the reactant gas mixture has an $H_2$ to carbon oxide ratio from 1 to 10, and wherein the gas flow rate generates a Weight Hourly Space Velocity from 0.1 scc/gcat/h to 100 scc/gcat/h.

\* \* \* \* \*